United States Patent [19]
Krivan et al.

[11] Patent Number: 5,466,681
[45] Date of Patent: Nov. 14, 1995

[54] RECEPTOR CONJUGATES FOR TARGETING PENICILLIN ANTIBIOTICS TO BACTERIA

[75] Inventors: Howard C. Krivan, Derwood, Md.; A. Lennart I. Blomberg, Lund, Sweden

[73] Assignee: MicroCarb, Inc., Gaithersburg, Md.

[21] Appl. No.: 180,397

[22] Filed: Jan. 12, 1994

Related U.S. Application Data

[63] Continuation of Ser. No. 484,568, Feb. 23, 1990, abandoned.
[51] Int. Cl.$^6$ .................. A61K 31/715; A61K 31/705; A61K 39/00
[52] U.S. Cl. .................. 514/54; 514/61; 514/26; 530/395; 530/403; 530/411; 530/813; 435/69.1
[58] Field of Search .................. 424/89, 92, 85.8, 424/85.91, 86, 87; 530/395, 403, 411, 813; 536/4.1, 5, 6.5, 16.8, 53; 514/54, 61, 26; 435/69.1

[56] References Cited

U.S. PATENT DOCUMENTS

| | | | |
|---|---|---|---|
| 4,429,008 | 1/1984 | Martin et al. | 424/1.21 |
| 4,464,360 | 8/1984 | Leffler et al. | 536/53 |
| 4,489,710 | 12/1984 | Spitler | 424/140.1 |
| 4,507,234 | 3/1985 | Kato et al. | 530/363 |
| 4,545,985 | 10/1985 | Pastan et al. | 424/180.1 |
| 4,569,789 | 2/1986 | Blattler et al. | 530/391.9 |
| 4,625,014 | 11/1986 | Senter et al. | 530/300 |
| 4,638,045 | 1/1987 | Kohn et al. | 530/323 |
| 4,657,849 | 4/1987 | Källenius et al. | 514/54 |
| 4,665,060 | 5/1987 | Mårdh et al. | 514/61 |
| 4,671,958 | 6/1987 | Rodwell et al. | 42/1.53 |
| 4,699,784 | 10/1987 | Shih et al. | 424/181.1 |
| 4,830,852 | 5/1989 | Marburg et al. | 514/54 |
| 4,859,769 | 8/1989 | Karlsson et al. | 536/53 |
| 4,873,088 | 10/1989 | Mayhew et al. | 424/450 |
| 5,217,715 | 6/1993 | Krivan et al. | 424/92 |
| 5,225,330 | 7/1993 | Ginsburg et al. | 435/7.32 |

OTHER PUBLICATIONS

Bock, K. et al., *J. Biol. Chem.* 260:8545–8551, 1985.
Jansen, F. K. et al., *Immunological Rev.* 62:185–216, 1982.
Karlsson, K., *Meth. Enzymol.* 138:212–220, 1987.
Karlsson, K., *Annu. Rev. Biochem.* 58:309–350, 1989.
Krivan, H. C. et al., *Proc. Natl. Acad. Sci. USA* 85:6157–6161, 1988.
Krivan, H. C. et al., *J. Biol. Chem.* 264:9283–9288, 1989.
Kyogashima, M. et al., *Arch. Biochem. Biophys.* 270:391–397, 1989.
Roberts, D. D. et al., *J. Biol. Chem.* 264:9289–9293, 1989.
Strömberg, N. et al., *FEBS Lett.* 232:193–198, 1988.
Thorpe, P. E. and W. C. J. Ross, *Immunological Rev.* 62:119–158, 1982.
Wells, M. A. and J. C. Dittmer, *Biochemistry* 2:1259–1263, 1963.
Young, W. W., Jr. and C. A. Borgman, *Meth. Enzymol.* 138:125–132, 1987.
Baron et al., *Chemical Abstracts* 98:29991h, 1983.
Bastardo et al., *Infect. Immun.* 29(3):1134–1140, 1980.
Citovsky et al., *Exp. Cell. Res.* 166:279–294, 1986.
Dahmen et al., *Carb. Res.* 138:17–28, 1985.
Dwyer et al., *Biochemistry* 21:3227–3231, 1982.
Goins et al., *Biochemistry* 24:1791–1797, 1985.
Haywood, *J. Mol. Biol.* 83:427–436, 1974.
Herrmann et al., *Biochemistry* 29:4054–4058, 1990.

(List continued on next page.)

*Primary Examiner*—Stephen G. Walsh
*Assistant Examiner*—Elizabeth C. Kemmerer
*Attorney, Agent, or Firm*—Pennie & Edmonds

[57] ABSTRACT

A variety of conjugates useful for the treatment of infections due to pathogenic microorganisms are provided. The conjugates comprise at least one agent coupled to a receptor which binds a microorganism. Suitable agents include anti-infectives, such as antibiotics and synthetic drugs. The present invention also provides methods for treating infections in warm-blooded animals due to pathogenic microorganisms.

10 Claims, 2 Drawing Sheets

OTHER PUBLICATIONS

Krivan et al., *Arch. Biochem. Biophys.* 260(1):493–496, 1988.

Mastromarino et al., *Med. Microbiol. Immunol.* 179(2):105–114, 1990.

Melikyan et al., *Chemical Abstracts* 112:19508z, 1990.

Ponpipom et al., *Can. J. Chem.* 58:214–220, 1980.

Sabesan et al., *Can. J. Cehm.* 62:644–654, 1984.

Tang et al., *Biochem. Biophys. Res. Commun.*, 132(2):474–480, 1985.

Willoughby et al., *J. Virol.* 64(10):4830–4835, 1990.

Asialo-GM1-Linker-Amoxicillin
Active Receptor Drug

RECEPTOR CONJUGATES FOR TARGETING PENICILLIN ANTIBIOTICS TO BACTERIA

This is a continuation of application Ser. No. 07/484,568, filed Feb. 23, 1990, now abandoned.

TECHNICAL FIELD

The present invention relates generally to conjugates comprising an agent, such as an anti-infective, coupled to a receptor which binds a microorganism, and to methods for making and using these conjugates.

BACKGROUND OF THE INVENTION

A reoccurring problem in medicine is that, due to the lack of specificity of the agents used for treatment of illnesses, the patient is often the recipient of a new set of maladies from the therapy. This scenario is common and has occurred in the treatment of infections due to pathogenic microorganisms.

The conventional approach to attempting to minimize adverse side-effects of an anti-microbial agent, such as a drug, to a patient has been to prepare a myriad of chemical derivatives in which moieties are added and/or deleted. The derivatives are then assessed for their effectiveness as well as their toxicity. Such an approach to minimizing adverse side-effects has been costly, time-consuming, and not always successful.

Due to the difficulties in the current approaches to the preparation of anti-microbial agents which exhibit minimal side effects, there is a need in the art for such agents. The present invention fills this need, and further provides other related advantages.

SUMMARY OF THE INVENTION

Briefly stated, the present invention provides a variety of conjugates useful for the treatment of infections due to pathogenic microorganisms. The microorganism receptor conjugates comprise at least one agent coupled to a microorganism receptor, the receptor being capable of selectively binding a microorganism. Preferred microorganisms include bacteria, viruses, mycoplasma, fungi and parasites.

In one embodiment, the conjugate includes an agent which is an anti-infective. Preferred anti-infectives include antibiotics, synthetic drugs and steroids. In another embodiment, the conjugate includes an agent which is a molecule that induces neutralization of the microorganism, for example, by stimulating the production of antibodies.

Within a related aspect, the present invention provides methods for the treatment of infections due to pathogenic microorganisms. In one embodiment, the method comprises administering to a warm-blooded animal an effective amount of a conjugate described above, wherein the microorganism receptor is capable of selectively binding a pathogenic microorganism. A preferred warm-blooded animal is a human.

These and other aspects will become evident upon reference to the following detailed description and attached drawings.

DETAILED DESCRIPTION OF THE INVENTION

Figure 1:
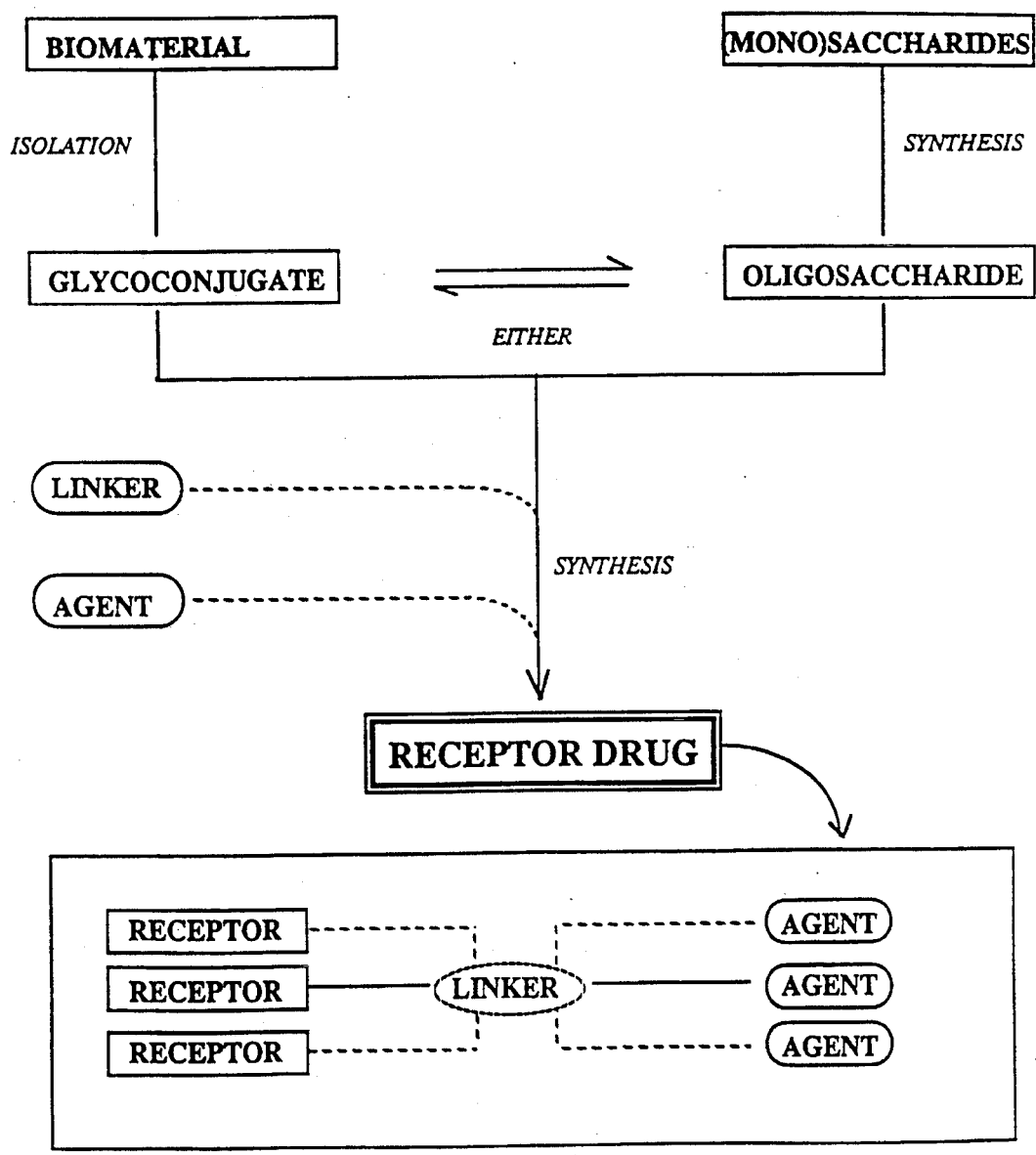
FIG. 1 depicts a flowchart illustrating a procedure for the preparation of microorganism conjugates of the present invention in which the agent portion is a drug.

As noted above, the present invention provides microorganism receptor conjugates and methods for using the conjugates for the treatment of infections due to pathogenic microorganisms. These conjugates, in which at least one agent is coupled to a receptor for a microorganism, have enormous potential as potent anti-microbial compositions. This is due to the selectivity imparted to the conjugate by the receptor portion. The selectivity of the receptor permits increased targeting and specificity for the pathogen. In addition, targeting of anti-microbial agents by using the conjugates of the present invention minimizes the dosage and adverse side-effects, such as the accumulation of toxic drugs in vital organs, in a patient.

Glycoproteins, proteins and glycolipids on a host cell may function as receptors for the recognition and attachment of microorganisms to the host cell. The active part of a glycoprotein or glycolipid receptor, i.e., the minimum binding epitope, appears generally to be the carbohydrate moiety. Alternatively, an epitope on a glycoprotein or protein may be formed from its amino acid residues. Therefore, the targeting portion ("microorganism receptor") of the conjugates of the present invention may comprise a glycolipid or carbohydrate moiety thereof; glycoprotein, glycopeptide or carbohydrate moiety of either; or protein or peptide. Microorganism receptors of the present invention include purified receptors or portions thereof, synthetically prepared receptors or portions thereof, and derivatives of receptors or portions thereof. A microorganism receptor is capable of selectively binding a microorganism. Recognition and attachment of microorganisms to host cells is the result of specific interactions, between molecules on the microorganisms and microorganism receptors on the host cells, that permit the receptors to selectively bind microorganisms. Representative microorganisms include bacteria, viruses, mycoplasma, fungi and parasites. More than one pathogenic microorganism may bind to the same epitope, e.g., carbohydrate sequence, in order to infect cells. Conversely, a microorganism may have unique receptor specificities. In either situation, a microorganism is infecting a host cell by selectively binding to a microorganism receptor.

Receptors for microorganisms may be purified from host cells by standard biochemical techniques. For example, glycolipids may be purified by the methods described by Karlsson (*Meth. Enzymol.* 138:212–219, 1987). Briefly, body fluid or cells are extracted with one or more organic solvents and the extract is subjected to mild alkaline degradation. Following neutralization and dialysis, the lipids and glycolipids are separated by a series of chromatography techniques, e.g., silicic acid and ion-exchange chromatography. The preparative steps are typically checked by thin-layer chromatography. (TLC). Purified, intact receptors may be used to prepare the conjugates of the present invention. Alternatively, it will be evident to one skilled in the art that, using chemical, and/or enzymatic, reagents and techniques, an intact receptor may be cleaved (to yield a portion thereof) and/or structurally modified (to yield a derivative of an intact receptor or portion thereof).

A representative example is the purification of asialogangliosides (Krivan et al., *Proc. Natl. Acad. Sci. USA*

85:6157–6161, 1988). Briefly, fucosylasialo-GM$_1$ and asialo-GM$_1$ were prepared from bovine brain gangliosides by hydrolysis in 25 mM H$_2$SO$_4$ for 1.5 hours at 80° C. The hydrolysis was neutralized with NH$_4$OH and dried under nitrogen, the residue was dissolved in chloroform/methanol/ water (60:30:4.5, vol/vol), and non-glycosphingolipid contaminants were removed by Sephadex G-25 column chromatography (Wells et al., *Biochemistry* 2:1259–1263, 1963). Fucosylasialo-GM$_1$ and asialo-GM$_1$ were separated from residual gangliosides by column chromatography on DEAE Sepharose and further purified by continuous thin-layer chromatography (Young et al., *Meth. Enzymol.* 138:125–132, 1987) on preparative silica gel G plates with chloroform/methanol/water (75:18:2.5, vol/vol) as the mobile phase. Asialo-GM$_2$ was obtained after digestion of asialo-GM$_1$ with bovine testes β-galactosidase (0.5 unit/ml) for 36 hours at 37° C. in 0.1M acetate buffer (pH 5.0) containing 0.2% sodium taurocholate. Polar contaminants and detergent were removed by Sephadex G-25 and DEAE-Sepharose column chromatography, respectively.

Alternatively, once the receptor structure has been identified, it may be prepared synthetically using chemical, and/or enzymatic, reagents and techniques. Similarly, the carbohydrate moiety of a receptor may be isolated from host cells or, following structural determination, prepared synthetically. Similar to the discussion above regarding purified receptors or portions thereof, structurally modified receptors or portions thereof may be prepared synthetically.

Briefly, in the case of enzymatic synthesis of carbohydrates, natural unprotected mono-, di- or oligo-saccharides and sialic acids are used as starting materials. Properly activated derivatives thereof in the anomeric center may have to be used. The glycoside synthesis is hereafter carried out with the help of specific enzymes. In the case of chemical synthesis, the same starting materials described above or derivatives thereof can be used. In this case, proper preactivation of the anomeric center together with proper specific protection of the remaining hydroxyls has to be performed prior to use in specific glycoside synthesis. For example, five hydroxyl groups of a hexose may be converted to —OR$_1$ through —OR$_5$, with R$_2$–R$_5$ representing protective groups. If the compound is used as the glycosyl donor, R$_1$ is a group that is suitable for activation in a glycoside synthesis by a different catalyst. Examples of such groups are halides, sulfur derivatives, acetimidates and orthoesters. Conversely, if the compound is used as the glycosyl acceptor, R$_1$ can be a protecting group as described below. R$_1$ can also be chosen in a way such that it can be converted in a later step into a group as described above. A third possibility is that R$_l$ is a ligand suitable for further coupling to other compounds.

Protecting groups from diverse arts may be employed when the derivative is used as the glycosyl donor. Commonly used protecting groups are, for example, acetyls, benzyls, benzoates and acetals. If the compound is used as the glycosyl acceptor, one or several of the hydroxyls is unprotected in order to render them accessible in the glycoside synthesis. It is well known in the art to choose the protecting groups such that the hydroxyls are selectively deblocked in order to continue an oligosaccharide synthesis. R$_2$–R$_5$ may also be other protected carbohydrate residues or other substituents or functional groups. The glycosyl donor and the glycosyl acceptor may be reacted together in the presence of a suitable catalyst to create the desired glycosidic bond. Depending on how the protecting groups, the anomeric group, the catalyst and the reaction condition are chosen, stereoselectivity and the desired stereochemistry can be obtained. If desired, this protected product can be deprotected to the free oligosaccharide. If further reactions are to be carried out, this can be done by proper selection of the starting materials which facilitates other glycosidation reaction by selectively manipulating the protecting groups and the anomeric center. This can be done both with a stepwise or a blockwise approach. The hydroxyl substituents may also be changed into other functional groups or attached to a ligand suitable for coupling.

In addition to a microorganism receptor, the conjugates of the present invention include at least one agent which directly or indirectly inhibits microorganisms. A variety of agents are suitable. For example, in one embodiment, one or more agents which are cytotoxic to a microorganism are coupled to a microorganism receptor to create a conjugate that may be termed a "receptor drug." Preferred agents are the classes of anti-infectives, such as antibiotics and synthetic drugs, that are efficacious in the treatment of infections due to pathogenic microorganisms. Representative antibacterial agents include aminoglycosides, polymyxins, sulfonamides, metronidizole, trimethoprim-sulfamethoxazole, and penicillins. A representative antiviral agent is acyclovir. Representative antifungal agents include amphotericin B, nystatin and 5-fluorocytosine. Representative antiparasitic agents include pentamidine and nitoimidazoles. Other agents which may be useful include steroids such as corticosteroids, e.g., prednisone, prednisilone and dexamethasone. The receptor drugs of the present invention provide an efficient drug targeting system that specifically eliminates pathogens by, for example, "fooling" the pathogen into binding to an artificial receptor (i.e. one coupled to a cytotoxic agent) rather than to a natural receptor on a host cell. Alternatively, pathogens may already be attached to host cells and the receptor drugs of the present invention may bind to the pathogens via, for example, extra, specific molecules on the pathogens that are not bound to the receptors.

The conjugates of the present invention, in another representative embodiment, include a molecule that induces neutralization of a microorganism. For example, the agent may be a molecule which stimulates the production of antibodies. Because, for example, carbohydrate receptors for pathogenic microorganisms are typically small and occur naturally on host cells, they are usually not immunogenic. However, a microorganism receptor can be coupled to a carrier molecule, such as keyhole limpet hemocyanin, that confers immunogenicity. Consequently, when a pathogenic microorganism binds to this type of receptor conjugate, the pathogen becomes attached via the receptor portion of the conjugate to a molecule which stimulates the production of antibodies by the host. Binding of antibodies to the pathogen via the conjugate sets in motion a sequence of events, the end result of which is neutralization of the pathogen.

An agent may be coupled to, i.e., covalently bonded to, a microorganism receptor either directly or via a linker group. A direct reaction between an agent and a receptor is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group, e.g., a halide, on the other.

Alternatively, it may be desirable to couple an agent and a receptor via a linker group. A linker group can function as a spacer to distance a receptor from an agent in order to avoid interference with binding capabilities, e.g., by steric hindrance or conformational changes. A linker group can also serve to increase the chemical reactivity of a substituent on an agent or a receptor, and thus increase the coupling efficiency. An increase in chemical reactivity may also facilitate the use of agents, or functional groups on agents, which otherwise would not be possible. A carboxyl group, for example, may be activated. Activation of a carboxyl group includes formation of an "active ester," such as a succinimidyl ester. The term "active ester" is known to refer to esters which are highly reactive in nucleophilic substitution reactions.

It will be evident to one skilled in the art that a variety of bifunctional or polyfunctional reagents, both homo- and hetero-functional (such as those described in the Pierce Chemical Co. catalog), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where an agent is more potent when free from the receptor portion of the conjugates of the present invention, it may be desirable to use a linker group which is cleavable, e.g., bio-cleavable. A number of different cleavable linker groups have been described previously. The mechanisms for release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to a microorganism receptor. In one embodiment, multiple molecules of an agent are coupled to one receptor molecule. In another embodiment, more than one type of agent may be coupled to one receptor. Regardless of the particular embodiment, conjugates with more than one agent may be prepared in a variety of ways. For example, receptors with multiple sites for attachment of agents can be coupled directly, or linkers which provide multiple sites for attachment can be used. Alternatively, a carrier can be used. A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome (e.g., U.S. Pat. Nos. 4,429,008 and 4,873,088).

As noted above, the present invention also provides a method of using the conjugates described above. The method comprises administering to a warm-blooded animal, such as a human, an effective amount of these conjugates. It will be evident to one skilled in the art that the site of infection will be the most important factor in determining not only the choice of the particular conjugate, but also the route by which it should be administered. For instance, a fungal infection of the skin may be treated by topical administration and a bacterial infection of the ears by oral administration. Methods of administration include oral, intravenous, intramuscular, topical and rectal. For oral administration, the conjugates may be in pill, capsule or liquid form. For any method of administration, the conjugates may be combined with a physiologically acceptable carrier or diluent, such as water or physiological saline.

By administering to a warm-blooded animal an effective amount of a conjugate of the present invention, treatment of an infection due to a pathogenic microorganism is effected. The causative agent of an infection may be bacteria, viruses, mycoplasma, fungi or parasites. Representative bacteria include the gram-negative, gram-positive, anaerobes, spirochetes, mycobacteria and actinomyces. Representative viruses include RNA and DNA viruses, e.g., herpes, cytomegalovirus, influenza, hepatitis, RSV and HIV. Representative mycoplasmataceae include *M. pneumonies, M. hominus*, Ureaplasma and Acoleplasma. Representative fungi include Candida, Cryptococcus, Coccidioides, Sporothrix, Aspergillus and Histoplaasma. Representative parasites include protozoa (e.g., *trhichomonas, pneumocystis* and *entomoeba*) and *helminths* (e.g., nematodes and trematodes). Other pathogenic microorganisms include the chlamydia/rickettsia group, e.g., *C. trachomatis, C. psittaci, C. pneumoniae* (TWAR), Rickettsia and Coxiella bacteria.

The mechanism by which a pathogenic microorganism is neutralized depends upon the type of agent in a particular conjugate. For example, certain agents, such as those which stimulate the production of antibodies, work in conjunction with existing host cell defense mechanisms. Alternatively, other agents, such as those which are cytotoxic, may inactivate the microorganism more directly.

The precise dose for a particular conjugate may vary, depending upon the agent and the receptor used. In particular, agents vary with respect to their potency and receptors vary with respect to binding affinity. Generally, however, an effective amount of a conjugate of the present invention will be from about 0.1 to about 10 mg per kg body weight. It will be evident to one skilled in the art how to determine the optimal effective dose for a particular conjugate. For example, the effective amount may be determined based upon in vitro experiments, followed by in vivo studies.

The particular conjugate administered is dependent on the nature of the infection or microorganism that is to be targeted. Determining the nature of an infection may be accomplished by a variety of known techniques, such as immunoassays using body fluids. In the embodiment where the agent is an antibiotic or synthetic drug, a compound which is efficacious for a particular infection is coupled to the appropriate receptor. For example, amoxicillin is used to treat pneumonia because it affects the growth of *Streptococcus pneumoniae*. In preparing a receptor drug for treating pneumonia, amoxicillin may be covalently coupled to asialo-$GM_1$ oligosaccharide, the carbohydrate structure which is the receptor for the organism. Other examples of receptor drugs within the present invention include a lactosylceramide-amphotericin B conjugate for use against fungi (e.g., Candida or Cryptococcus) and a sulfatide-tetracycline or sulfatide-erythromycin conjugate for use against mycoplasmas. Examples of the drugs currently of choice for representative microorganisms are listed in Table 1 below.

TABLE 1

| Drug of Choice | Microorganism | Class of Organism |
| --- | --- | --- |
| Amphotericin B | Candida, Cryptococcus | Fungi (yeast) |
| Metronidazole | Trichomonas | Protozoan |
| Amoxicillin | Helicobacter pylori (formerly Campylobacter pylori) | Bacteria |
| Ampicillin/Amoxicillin | Streptococcus pneumoniae | Bacteria |
| Tetracycline/ | Mycoplasma pneumoniae | Mycoplasma |

TABLE 1-continued

| Drug of Choice | Microorganism | Class of Organism |
|---|---|---|
| Erythromycin | | |
| Tetracycline | *Chlamydia trachomatis* | Bacteria |
| Acyclovir/Ganciclovir | Herpes/ Cytomegalovirus | Virus |

The following examples are offered by way of illustration and not by way of limitation.

EXAMPLES

Example 1

Preparation of Asialo-GM$_2$-Amoxicillin

A. Preparation of Asialo-GM$_2$-Oligosaccharide

Melting points are corrected. Reactions were performed under nitrogen. Concentrations were performed at <40° C. (bath). Optical rotations were recorded at 25° C. with a Perkin-Elmer 241 polarimeter. Thin-layer chromatography was performed on silica gel 60 F$_{254}$ (Merck, Darmstadt, FRG) using the following eluant systems: A, 4:3:3:2 ethyl acetate: acetic acid: methanol: water, B, 10:5:1 chloroform: methanol: water, C, 11:9:2 chloroform: methanol: water. The spots were visualized by charring with 5% aqueous sulfuric acid. Silica gel chromatography was performed on Matrex silica Si, 60A, 20–45 MY (Amicon Corporation, Danvers, Mass. 01923, U.S.A.), using solvent system D, 5:1 methylene chloride: pyridine and E, 10:5:3:1:1 chloroform: methanol: dioxane, water: pyridine, Sulfuryl chloride/triflic acid reagent was made 1M in toluene containing 10% diethylether. Organic solvents were of p.a. quality and distilled over appropriate drying agents.

p-Methylphenyl 3,4,6-tri-O-p-chlorobenzyl-2-deoxy-2-phthalimido-1-thio-β-D-galactopyranoside (1):

Into a stirred solution of p-methylphenyl-2-azido-3,4,6-tri-O-chlorobenzyl-2-deoxy-1-thio-β-D-galactopyranoside (5.00 g) in 1:1 pyridine/triethylamine (200 ml) at room temperature was bubbled H$_2$S until saturation. The flask was sealed and stirring was continued for 2 hours. Then nitrogen was flushed through the solution, and phtalic anhydride (3.0 g) in methylene chloride (100 ml) was added. The mixture was stirred overnight. Then acetic anhydride (50 ml) in toluene (100 ml) was added. After 2 hours, water (50 ml) was added. The organic phase was washed with water, saturated sodium bicarbonate and 1 M sulfuric acid and evaporated. The resulting syrup was chromatographed in 7/1 toluene/ethyl acetate. Crystallization of appropriate fractions from diethylether/isooctane gave pure (1) (3.89 G, 67.5%), mp 63°–70° C., [α]$_D$+70.1° (c 1.0 chloroform).

Ethyl 4-O-β-galactopyranosyl-1-thio-β-D-glucopyranoside (2):

To a mixture of β-lactose peracetate (50 g), ethanethiol (6.9 g, 822 ml) and 200 ml dry CH$_2$Cl$_2$ was added BF$_3$/Et$_2$O (8.5 g, 7.3 ml) at RT. After 2 hours, TLC (toluene/ethyl acetate 2/3) showed no more reaction. The mixture was shaken with ca 500 ml 1M NaOH. The organic layer was directly evaporated and taken up in methanol (150 ml), then NaOMe in methanol (10 ml, 0.5M) was added and the mixture was stirred overnight at RT. The TLC (ethyl acetate/ acetic acid/methanol/water 12/3/3/3) yields an Rf 0.41. The reaction mixture was neutralized with Dowex (50w×8, H$^+$) filtered and concentrated The residue was recrystallized from ethanol (300 ml). Yield 16.4 g, 56%, mp 191°–192° C.

Ethyl 4-O-(4,6-O-benzylidene-β-D-galactopyranosyl)-1-thio-β-D-glucopyranoside (3):

A mixture of (2) (3.00 g) and bensaldehyde (30 ml) was stirred for 1 hour at room temperature. Then formic acid (30 ml) was added, and stirring was maintained for a further 25 minutes. The clear solution was poured into diethylether (400 ml) during stirring. After 1 hour, the solid was filtered off and dissolved in methanol (50 ml) during heating. After cooling diethylether (25 ml) was added. Crystals were obtained after standing overnight (3.09 g, 84%), 240°–242° C., [α]$_D$–49.3°.

Ethyl 4-O-(4,6-O-benzylidene-2,3-di-O-p-chlorobenzyl-β-D-galactopyranosyl-2,3,6-tri-O-p-chlorobenzyl- 1-thio-β-D-glucopyranoside (4):

Treatment of (3) (2.00 g) with p-chlorobenzyl chloride (3.0 ml) and sodium hydride (1.4 g) in DMF (50 ml) at 0° C. under nitrogen gave a single spot on TLC (toluene/ethyl acetate 4/1, Rf 0.39). Partitioning between toluene and 1M sulfuric acid and water, and crystallization from dichloromethane/ethyl acetate/isooctane gave 3.57 g (4), 77%, mp 179°–183° C., [α]$_D$+10.9° (c 1.0, chloroform).

Ethyl 4-O-(6-O-benzyl-2,3-di-O-p-chlorobenzyl-β-D-galactopyranosyl)-2,3,6-tri-O-p-chlorobenzyl- 1-thio-β-D-glucopyranoside (5):

Compound (4) (100 mg) in THF (10 ml) containing molecular sieves 3 Å) 600 mg) at room temperature under nitrogen was treated with NaCNBH$_3$ (100 mg) and HCl (saturated in diethyl ether) as described. After 2 hours, TLC (toluene/ethyl acetate 4/1, Rf 0.55) showed complete reaction. The mixture was filtered, partitioned between dichloromethane and sodium bicarbonate and water. Pure (5) was obtained after crystallization from ethyl acetate/isooctane (82 mg, 82%), mp 137°–139° C., [α]$_D$+25.6°.

2-(p-Nitrophenyl)ethyl 4-O-(6-O-benzyl-2,3-di-O-p-chlorobenzyl-β-D-galactopyranosyl)- 2,3,6-tri-O-p-chlorobenzyl-β-D-glucopyranoside (6):

A solution of (5) (500 mg) in methylene chloride (20 ml) was treated with bromine (50μ) and molecular sieves 4 Å (5.0 b) at 0° C. during stirring. After 30 minutes, TLC (toluene/ethyl acetate 4/1) indicated that no starting material remained, and excess bromine was destroyed with two drops of cyclohexene. The slurry was added dropwise to a stirred mixture of 2-(4-nitrophenyl)-ethanol (300 mg) and freshly activated zinc chloride (5.0 g) in methylene chloride (10 ml), while maintaining nitrogen atmosphere and 0° C. After two hours, the mixture was diluted with methylene chloride, filtered, washed with water and 1M sulfuric acid, dried and concentrated. The resulting syrup was chromatographed in isooctane/ethyl acetate 1/1. Fractions containing pure material of Rf 0.53 was pooled and concentrated (340 mg, 62%). Nmr analysis showed this to be the desired (6). Crystals of (6) were obtained from diethyl ether/isooctane, mp 110°–112° C., [α]$_D$+22.8°.

2-(p-Nitrophenyl)ethyl 4-O-(3,4,6-tri-O-p-chlorobenzyl-2-deoxy-2-phthalimide-β-D-galactopyranosyl) 1-O-(6-O-benzyl-2,3-di-O-p-chlorobenzyl-β-D-galactopyranosyl)-2,3,6-tri-O-p-chlorobenzyl-β-D-glucopyranoside (7):

To an ice cooled solution of disaccharide (6) (71 mg, 1 eq) and thioglycoside (1) (58 mg, 1.2 eq) in dry methylene chloride (5.0 ml) containing molecular sieves 4 Å (100 mg) was added SO$_2$Cl$_2$/HOTf reagent (0.30 ml, 5 eq) under nitrogen during stirring. The mixture was stirred for 2 hours during which the temperature was allowed to rise to 10° C. Then pyridine (100 μl) was added and the mixture was stirred for another hour at room temperature. The mixture was filtered, partitioned between ethyl acetate and aqueous sodium bicarbonate, dried (MgSO$_4$) and concentrated. After silica gel chromatography in toluene/ethyl acetate 59% of (7) was obtained.

2-(p-Nitrophenyl)ethyl 4-O-(3,4,6-tri-O-p-chlorobenzyl-2-acetamido-2-deoxy-β-D-galactopyranosyl)- 4-O-(6-O-benyl-2,3-di-O-p-chlorobenzyl-β-D-galactopyranosyl)-2,3,6-tri-O-p-chlorobenzyl-β-D-glucopyranoside (8):

To a stirred solution of trisaccharide (7) (400 mg) in toluene/95% ethanol, 1/10 (10 ml) was added hydrazine hydrate (0.3 ml) and acetic acid (0.2 ml). The mixture was refluxed overnight, cooled, concentrated and co-evaporated with toluene/ethanol. The residue was treated with acetic anhydride/pyridine 1/1 (5 ml) for 30 minutes at room temperature. Concentration, partitioning between toluene and water, drying (MgSO$_4$) and concentration gave a syrup. The syrup was chromatographed on silica gel in n-heptane/ethyl acetate 1/1 (Rf 0.35). Appropriate fractions were pooled and concentrated to give (8) in 52% yield.

2-(p-Trifluoroacetamidophenyl)ethyl 4-O-(2-acetamido-2-deoxy-β-D-galactopyranosyl)- 4-O-β-D-galactopyranosyl-β-D-glucopyranoside (9):

To compound (8) (50 mg) in THF (2 ml), acetic acid (1 ml) and water (0.1 ml) was added zinc dust (100 mg) and the mixture was stirred at 0° C. under nitrogen. Then a solution of CuSO$_4$×5 H$_2$O (100 mg.ml, 0.2 ml) was added. After 30 minutes TLC (n-heptane: ethyl acetate 1:1, Rf 0.28) showed complete reaction. The mixture was filtered, diluted with CH$_2$Cl$_2$, washed with aqueous sodium bicarbonate, water, dried (MgSO$_4$) and concentrated. The residue was dissolved in CH$_2$Cl$_2$ (3 ml). The solution was cooled to 20° C. and pyridine (40 μl) and trifluoroacetic anhydride (20 μl) were added. After 10 minutes TLC (n-heptane: ethyl acetate 1:1, Rf 0.13) showed complete reaction. The mixture was concentrated to dryness and dissolved in ethyl acetate: ethanol: acetic acid: water 4:2:1:1 containing sodium acetate (50 mg) and hydrogenolyzed over Pd/C (10%, 50 mg) at atmospheric pressure for 8 hours as described. Complete debenzylation was indicated by TLC (ethyl acetate/methanol/acetic acid/water, 12/3/3/2, Rf 0.15). Purification by C-18 chromatography as described before gave 80% of (9). The structures of compounds (1) to (9) are shown below.

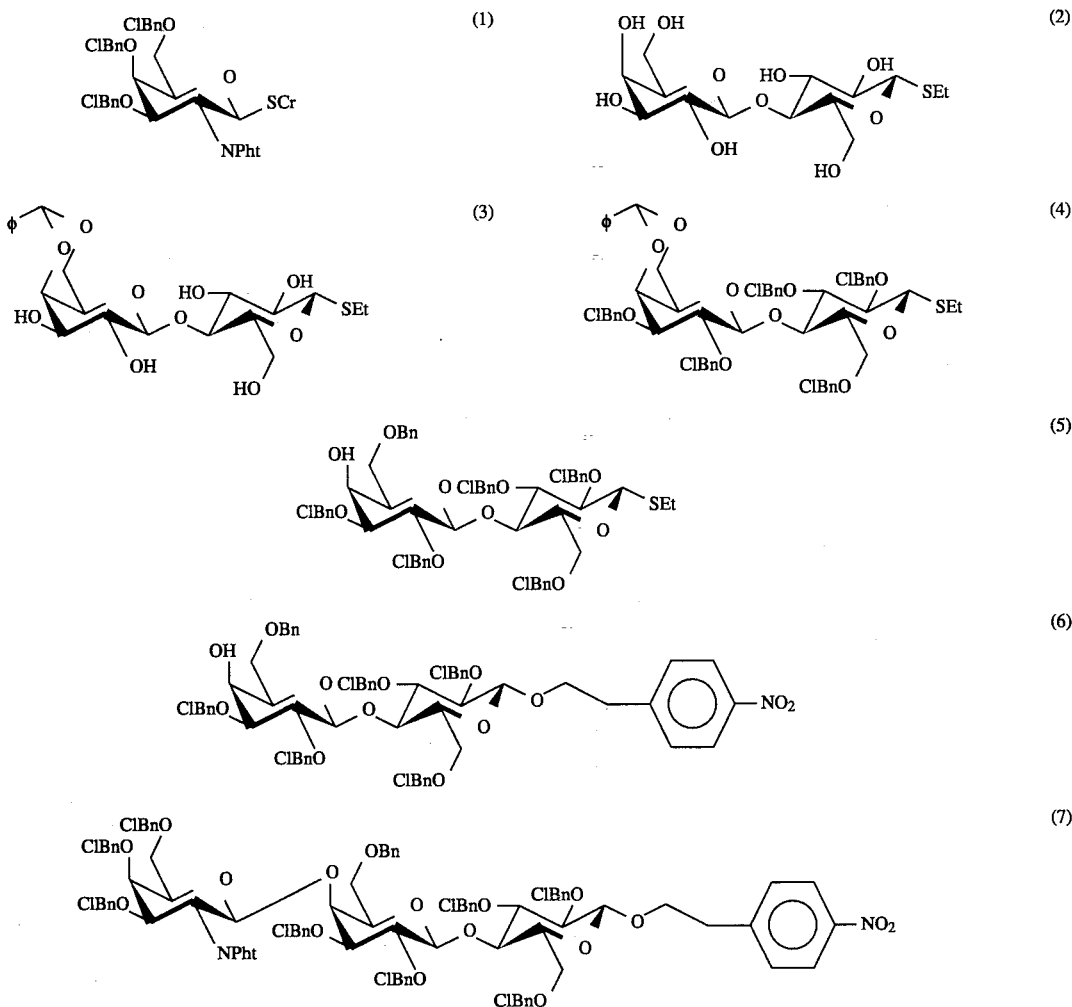

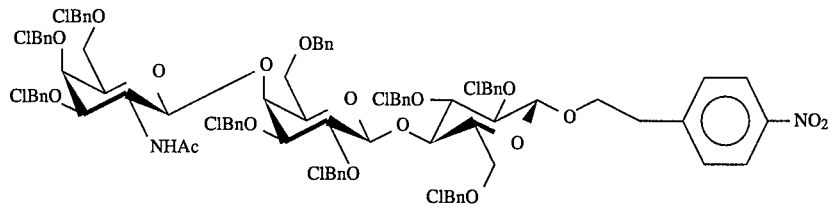

(8)

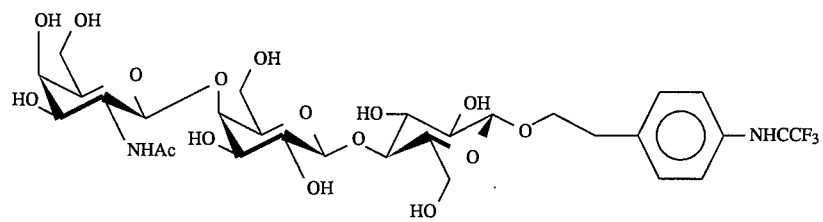

(9)

B. Preparation of Asialo-GM$_2$ Oligosaccharide-Amoxicillin 2-(p-Aminophenyl)ethyl 4-O-(2-acetamido-2-deoxy-β-D-galactopyranosyl)- 4-O-β-D-galactopyranosyl-β-D-glucopyranoside (10):

100 mg of compound (9) is dissolved in 10 ml 25% ammonia at 50° C. The mixture was left for an hour and is then put directly on a C 18 column and washed with water until the pH reaches about 9. The column was then eluted with 30% methanol. Ninhydrin positive fractions were pooled and partly evaporated to remove the bulk of methanol. The remaining solution was subjected to freeze-drying which gave a white fluffy powder pure by TLC. The yield is 95%.

2-(p-iso-Thiocyanatophenyl)ethyl 4-O-(2-acetamido-2-deoxy-β-D-galactopyranosyl)- 4-O-β-D-galactopyranosyl-β-D-glucopyranoside (11):

100 mg of compound (10) is dissolved in 10 ml 70% ethanol at room temperature. To the solution is added a twofold excess of thiophosgen and the solution is stirred for five minutes. After that enough ion exchanger is added to rise the pH to about 5 (Dowex 1×2 OH form). The ion exchange is then filtered off and washed with water. The filtrate is evaporated to remove most of the ethanol. The remaining solution is then freeze-dried to dryness which leaves a white powder essentially pure by TLC and NMR. The yield is about 50%.

2-(p-Amoxicillin thiourea phenyl) ethyl 4-O-(2-acetamido-2-deoxy-β-D-galactopyranosyl)- 4-O-β-D-galactopyranosyl-β-D-glucopyranoside (12):

50 mg of compound (11) is dissolved in 5 ml DMF. An equimolar amount of Amoxicillin is added and the solution is left for two days at room temperature which gives a clear yellow solution. On TLC (EtOAc:MeOH:H$_2$O:HOAc 12:3:3:2) only traces of the reactants can be seen and one major product together with small amounts of byproducts. The solvent is evaporated with the help of a vacuum pump slightly above room temperature. The remaining solid is dissolved in water and chromatographed on a C 18 column. It is first eluted with water and thereafter with 30% methanol. The desired fractions are pooled and freeze-dried after evaporation of the methanol. The structure of the substance is confirmed by NMR and FAB/MS. The yield is 62%. The structures of compounds (9) to (12) are shown below.

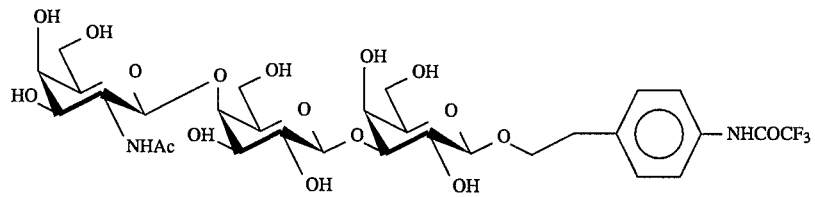

(9)

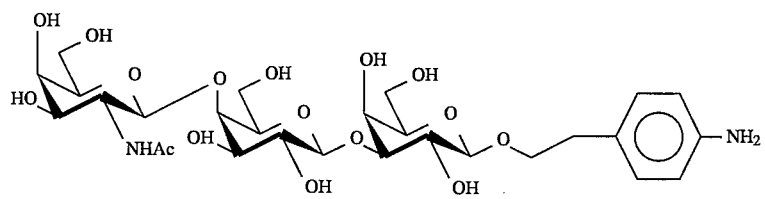

(10)

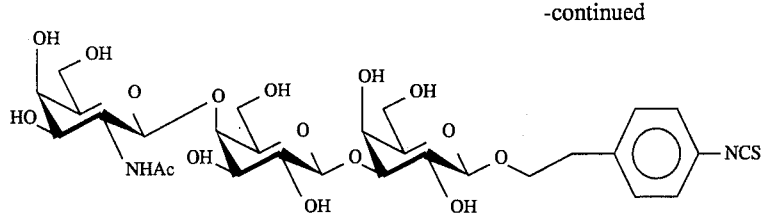

(11)

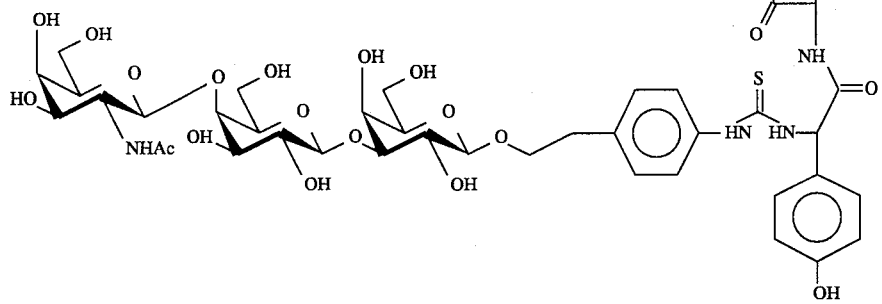

(12)

EXAMPLE 2

Preparation of Asialo-$GM_1$-Amoxicillin

A. Asialo-$GM_1$

Asialo-$GM_1$ can be purified from gangliosides as described above or purchased (BioCarb Chemicals, Lund, Sweden).

B. Preparation of Asialo-$GM_1$-Amoxicillin Using A Hetero-Bifunctional Reagent

Figure 2:
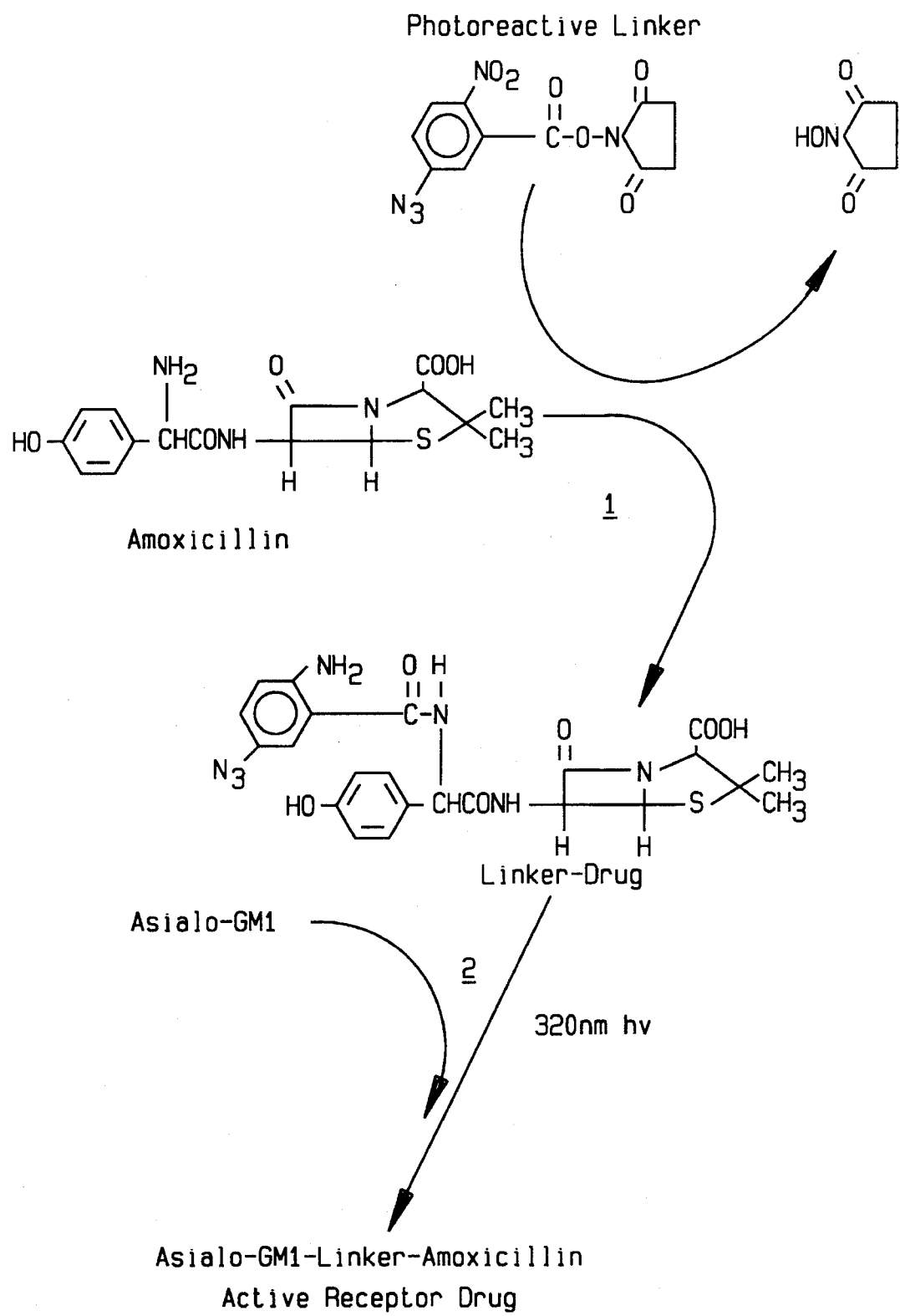
FIG. 2 shows a diagram illustrating the crosslinking of amoxicillin to the glycolipid receptor asialo-$GM_1$ using a photoreactive linker.

Asialo-$GM_1$ (BioCarb Chemicals, cat. #65/03) and other relevant glycolipids are made to a concentration of 10 mg/ml in HPLC-grade dimethylsulfoxide (DMSO) and stored at 4° C. until use. The photo-heterobifunctional reagent ANB-NOS (Pierce, cat. #21551) is dissolved in the dark in HPLC-grade DMSO at a concentration of 300 mg/ml and stored in the dark at 4° C. until use. Amoxicillin (Sigma, cat. #A-8523, lot: #29F0730) is dissolved in DMSO to a concentration of 120 mg/ml. In the dark, ANB-NOS-DMSO and Amoxicillin-DMSO are mixed in a 1:1 ratio (wt/wt) and incubated at room temperature for one hour (step 1 in FIG. 2). After this incubation in the dark, asialo-$GM_1$ is added to the reaction mixture in a ratio of 12:1 ANB-NOS-Amoxicillin to asialo-$GM_1$. The reaction mixture is exposed to a sunlamp (G.E. bulb #RSM-6) for 15 minutes where the reaction mixture will change from yellow to amber resulting in Amoxicillin-Asialo-$GM_1$ (step 2 in FIG. 2). The reaction is approximately 30%–50% efficient.

EXAMPLE 3

Inhibition of Streptococcus pneumoniae by Asialo-$GM_1$, Amoxicillin In Vitro

Determination of the minimum inhibitory concentration (MIC) was done according to recommendations published by the National Committee for Clinical Laboratory Standards (Tentative Standard NCCLS Publication M7-T2, Villanova, Penn., NCCIS, 1988). Both amoxicillin and amoxicillin-asialo-$GM_1$ (prepared according to Example 2) were tested for bacteriostatic and bacteriocidal levels using a clinical isolate of Streptococcus pneumoniae. Stock solutions of amoxicillin and amoxicillin-asialo-$GM_1$ were diluted to 10 µg/ml in Trypticase soy broth without glucose (T-soy from Difco). Serial two-fold dilutions were made from stocks in a series of 16 tubes each containing 1 ml of medium such that tube 1 contained 5 µg/ml through tube 16 which contained 0.0001 µg/ml of antibiotic. To each of these tubes was added 0.05 ml of a suspension of S. pneumoniae (approximately $1.5 \times 10^8$) organisms/ml using a 0.5 McFarland standard. T-soy broth with no organisms and with organisms and no antibiotics served as negative and positive controls, respectively. All tubes were incubated at 37° C. in 5% $CO_2$/95% air for 18 hours and read for turbidity and MIC. For determination of bacteriocidal levels (MBC), 0.001 ml was taken from each tube showing no visible growth, inoculated onto 5% sheep blood agar plates and incubated an additional 18 hours. A 99% reduction in colony count compared to control tubes was considered bacteriocidal (MBC). The results of the comparison of amoxicillin and amoxicillin-asialo-$GM_1$ are shown in Table 2.

TABLE 2

Comparison of amoxicillin and amoxicillin-asialo-$GM_1$ against Streptococcus pneumoniae as measured by minimum inhibitory concentration (MIC) and minimum bacteriocidal concentration (MBC).

| Drug | MIC (ug/ml) | MBC (ug/ml) |
|---|---|---|
| Amoxicillin | 0.04 | 0.04 |
| Amoxicillin-Asialo-$GM_1$* | 0.005 | 0.005 |

*Prepared using an ANB-NOS-Amoxicillin to glycolipid ratio of 1:1

EXAMPLE 4

Inhibition of *Helicobacter pylori* In Vivo

Clinical studies suggest that Helicobacter Pylori-Like Organisms (HPLO) may cause duodenal ulcers, gastritis and hypochlorhydria. Moreover, HPLO may be responsible for unexplained vomiting in man. Several studies in Rhesus monkeys have demonstrated the presence of organisms closely resembling HPLO found in humans. In the monkeys used in this experiment, small curved rod-shaped bacteria measuring 3–4 μm long and 0.5–10.0 μm wide were seen in close proximity to the mucosal epithelial cells in 8/29 monkeys. These bacteria were very similar to *H. pylori* observed in humans and were therefore called GCLO. The effect of these bacteria on radiation induced vomiting and gastric suppression is unknown.

It is interesting that, although gastritis is known to be associated with gastric ulcer, duodenal ulcers and gastric cancer, its treatment remains symptomatic, and little if any improvements is observed after administration of typical antacids and/or histamine $H_2$ antagonists. In contrast, administration of bismuth salts and of several antibiotics has improved gastritis, while eradicating HPLOs. However, the prolonged use of large doses of antibiotics may lead to eradication of the normal flora and to the development of bacterial resistance and recurrence of infection is extremely frequent.

Two domestic born male rhesus monkeys, Macaca Mulatta in which HPLO is present in gastric biopsies and weighing 3–7 kg, were housed in individual stainless steel cages in conventional holding rooms of an AALAC accredited animal facility. The two infected monkeys were treated by administering blindly and t.i.d. either placebo or 7 mg/kg of asialo-$GM_1$-amoxicillin (prepared according to Example 2) diluted in Tang, a drink that is avidly consumed by monkeys and allows reliable oral administration of medications. The animals were treated for two days only, but HPLO were cultured only from gastric biopsies obtained immediately after the end of the treatment in the animal receiving placebo and not in the one treated with the receptor conjugate.

From the foregoing, it will be evident that, although specific embodiments of the invention have been described herein for purposes of illustration, various modifications may be made without deviating from the spirit and scope of the invention.

We claim:

1. A microorganism receptor-antibiotic conjugate, comprising an asialoganglioside coupled to a penicillin antibiotic, wherein said asialoganglioside selectively binds a microorganism which is a bacterium.

2. The microorganism receptor-antibiotic conjugate of claim 1, wherein said asialoganglioside is asialo-$GM_1$.

3. The microorganism receptor-antibiotic conjugate of claim 1, wherein said asialoganglioside is asialo-$GM_2$.

4. The microorganism receptor-antibiotic conjugate of claim 1, 2 or 3, wherein said penicillin antibiotic is amoxicillin.

5. A method for treatment of a bacterial infection, comprising administering to an animal an effective amount of a microorganism receptor-antibiotic conjugate, wherein said treatment attenuates or cures said infection, said conjugate comprises an asialoganglioside coupled to a penicillin antibiotic, and said asialoganglioside selectively binds a microorganism which is a bacterium.

6. The method for treatment of a bacterial infection of claim 5, wherein said asialoganglioside is asialo-$GM_1$.

7. The method for treatment of a bacterial infection of claim 5, wherein said asialoganglioside is asialo-$GM_2$.

8. The method for treatment of a bacterial infection of claim 5, 6 or 7, wherein said penicillin antibiotic is amoxicillin.

9. The method for treatment of a bacterial infection of claim 6, wherein said penicillin antibiotic is amoxicillin and said bacterial infection is by *Streptococcus pneumoniae*.

10. The method for treatment of a bacterial infection of claim 6, wherein said penicillin antibiotic is amoxicillin and said bacterial infection is by *Helicobacter pylori*.

* * * * *